(12) United States Patent
Heo

(10) Patent No.: US 10,031,587 B2
(45) Date of Patent: Jul. 24, 2018

(54) ELECTRONIC DEVICE

(71) Applicant: Samsung Electronics Co., Ltd., Gyeonggi-do (KR)

(72) Inventor: Joon Heo, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 51 days.

(21) Appl. No.: 14/887,593

(22) Filed: Oct. 20, 2015

(65) Prior Publication Data

US 2016/0109959 A1 Apr. 21, 2016

(30) Foreign Application Priority Data

Oct. 20, 2014 (KR) ........................ 10-2014-0142127

(51) Int. Cl.
| | |
|---|---|
| G06F 3/01 | (2006.01) |
| G06F 1/16 | (2006.01) |
| G06F 1/32 | (2006.01) |
| G06F 3/03 | (2006.01) |
| A61B 5/00 | (2006.01) |
| A61B 5/1455 | (2006.01) |

(52) U.S. Cl.
CPC .......... *G06F 3/017* (2013.01); *A61B 5/14551* (2013.01); *A61B 5/6898* (2013.01); *G06F 1/1626* (2013.01); *G06F 1/1684* (2013.01); *G06F 1/3231* (2013.01); *G06F 1/3265* (2013.01); *G06F 3/0304* (2013.01); *G06F 2203/0338* (2013.01); *Y02B 60/1242* (2013.01); *Y02B 60/1289* (2013.01); *Y02D 10/153* (2018.01); *Y02D 10/173* (2018.01)

(58) Field of Classification Search
CPC .......... G06F 3/017; G06F 3/015; G06F 21/32; A61B 5/6898; A61B 5/14551; A61B 5/024

See application file for complete search history.

(56) References Cited

U.S. PATENT DOCUMENTS

| | | | | |
|---|---|---|---|---|
| 2006/0009698 | A1* | 1/2006 | Banet | A61B 5/0205 600/485 |
| 2009/0117935 | A1* | 5/2009 | Gredvall | H04W 52/027 455/550.1 |
| 2010/0240402 | A1* | 9/2010 | Wickman | H04M 1/57 455/466 |
| 2010/0295781 | A1* | 11/2010 | Alameh | G06F 3/017 345/158 |
| 2010/0308958 | A1* | 12/2010 | Kim | G06F 3/017 340/5.1 |

(Continued)

FOREIGN PATENT DOCUMENTS

JP 2011-151596 A 8/2011

*Primary Examiner* — Thomas Alunkal
(74) *Attorney, Agent, or Firm* — Cha & Reiter, LLC

(57) ABSTRACT

An electronic device and method are disclosed, the electronic device including a variable detection module operable in a plurality of modes, each of the plurality of modes configuring the variable detection module to detect a different external signal; and a controller. The controller may implement the method, including operating the variable detection module in one of the plurality of operating modes, and executing a function of the electronic device in response to a signal detected by the variable detection module.

19 Claims, 8 Drawing Sheets

(56) References Cited

U.S. PATENT DOCUMENTS

| | | | |
|---|---|---|---|
| 2014/0357963 A1* | 12/2014 | Chang | A61B 5/6898 |
| | | | 600/301 |
| 2015/0062594 A1* | 3/2015 | Hwang | G06K 9/2018 |
| | | | 356/614 |
| 2015/0190093 A1* | 7/2015 | Chang | A61B 5/6898 |
| | | | 600/301 |

* cited by examiner

ELECTRONIC DEVICE

CLAIM OF PRIORITY

This application claims priority under 35 U.S.C. § 119(a) to Korean Application Serial No. 10-2014-0142127 filed in the Korean Intellectual Property Office on Oct. 20, 2014, the entire disclosure of which is hereby incorporated by reference.

TECHNICAL FIELD

The present disclosure relates to an electronic device, and more particularly, to an electronic device including various modules.

BACKGROUND

Typically, an electronic device may be configured to execute specific function corresponding to program installed within the device, and may include commonly used devices such as home appliances, electronic diaries, portable multimedia players, mobile communication terminals, tablet PCs, multimedia units, desktop/laptop computers, navigation units for vehicles, and other similar devices. In recent years, a large variety of these functions have been integrated into a single electronic device, such a tablets and a mobile communication terminals known as "smartphones." For example, programs for executing games, multimedia playback, communication, security, network enabled banking, scheduling, and even electronic wallet and payment functions have been integrated into a single electronic device Even functions such as biometric sensing have been incorporated.

SUMMARY

An electronic device is provided with various sensors and a light emitting unit. For example, the electronic device may include a gesture sensor, such as a proximity sensor, which may be mounted on a periphery of a display unit disposed on a front surface of the electronic device. The electronic device may also include an LED indicator (referred to as 'a service light' or 'a service light source') that displays to a user various signals via an LED light. Further, a body signal sensor (e.g., a biometrics sensor) may also be installed in the same electronic device. The body signal sensor may include, for example, a Heart Rate Monitor (HRM) sensor configured to measure a heart rate of a user of the electronic device.

Because these diverse sensors are disposed at separate mounting locations within or on the electronic device, each mounting location should securely fasten the respective sensor.

Furthermore, increasing the functionality of the electronic device by adding all these diverse sensors naturally increases the number of components, which increases material costs for manufacturing, due to the added cost of the component sensors, and the increased complexity of assembly during manufacturing.

In addition, in some configurations, the service light, the gesture sensor, and the body signal sensor may be installed as to be exposed on a case of the electronic device, which may reduce the aesthetic appeal and luxuriousness of the overall shape and design, or restrict it to some extent.

Accordingly, the various modules that may be mounted on the electronic device may include sub-modules presenting similar issues in terms of mounting.

For example, the HRM sensor may include a transmitter and a receiver, and the transmitter may include a red light source (hereinafter, referred to as 'RED LED') and an infrared light source (hereinafter, referred to as 'IR LED'), and the receiver may include a photo diode.

The structure of the HRM sensor may be similar to the structure of the LED indicator and the gesture sensor. The service sensor may emit RGB light (i.e., red, green, and blue light) and thus may correspond to the RED LED of the transmitter. Further, the transmitter and the receiver of the gesture sensor may correspond to an IR LED of the HRM sensor and the photo diode.

Accordingly, the present disclosure provides an electronic device including a variable detection module in which modules having similar structures and functions are integrated, and the function of the variable detection module may be alterable according to environment or user intention.

The present disclosure also provides an electronic device including a variable detection module allowing alteration of detection function according to a user setting. The variable detection module may include at least one light source, at least one receiver and at least one transmitter, the operation of which allows detecting a diversity of signals when operated in different detection modes.

In one aspect of the present disclosure, an electronic device including a variable detection module operable in a plurality of modes, each of the plurality of modes configuring the variable detection module to detect a different external signal, and a controller configured to operate the variable detection module in one of the plurality of operating modes.

In one aspect of the present disclosure an electronic device is disclosed including a variable detection module operable in a plurality of modes, each of the plurality of modes configuring the variable detection module to detect a different external signal; and a controller. The controller is configured to operate the variable detection module in one of the plurality of operating modes, and execute a function of the electronic device in response to a signal detected by the variable detection module.

According to various embodiments of the present disclosure, a detection module provided in the electronic device can be driven in two or more modes according to a user configuration setting. For example, in a first mode, the detection module may display a state of the electronic device, and motions and/or gestures can be detected. In a second mode, biometric information of the user of the electronic device may be detected.

Because diverse functions of the electronic device can be implemented through a single detection module, less space is required within or on the electronic device for mounting a plurality of modules. Consequently, material costs can be reduced, and the number of processes during assembly can also be reduced.

BRIEF DESCRIPTION OF THE DRAWINGS

The present disclosure will be more apparent from the following detailed description taken in conjunction with the accompanying drawings, in which.

DETAILED DESCRIPTION

Figure 1:
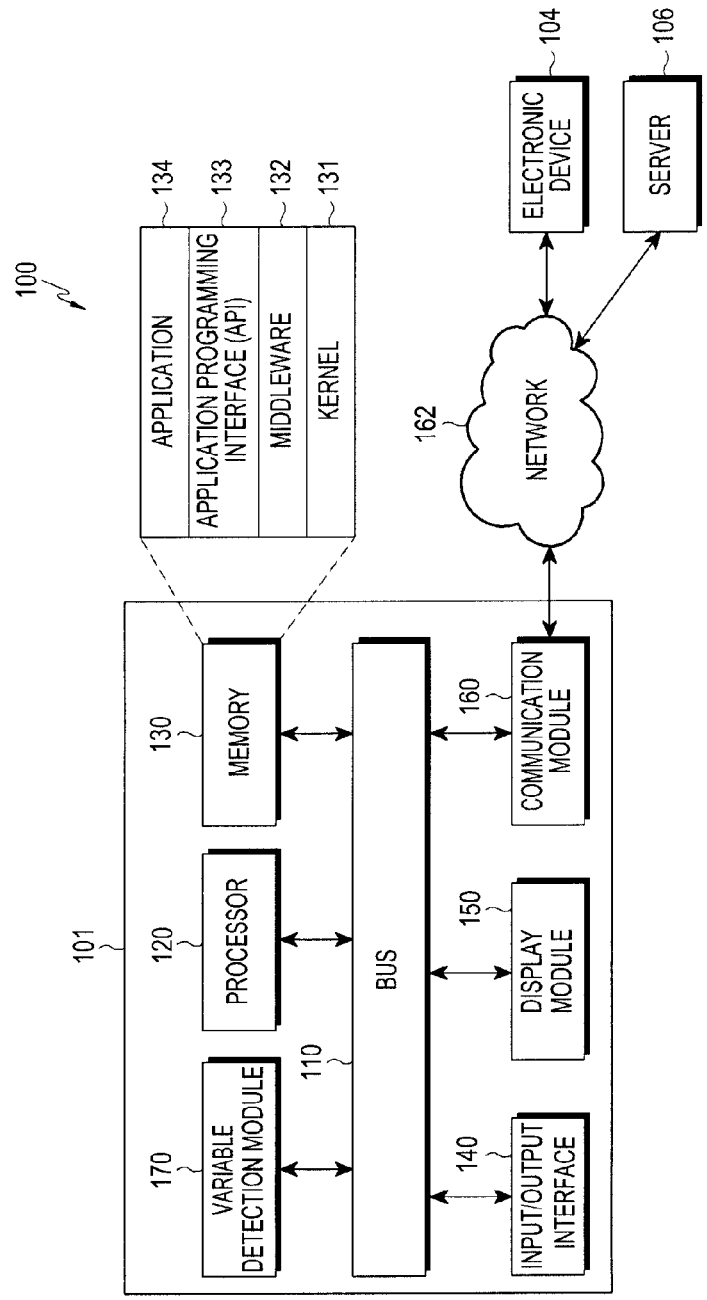
FIG. 1 illustrates a network environment including an electronic device according to various embodiments of the present disclosure.

Various embodiments of the present disclosure will now be described more fully in conjunction with the accompanying drawings. The present disclosure may have various embodiments, and modifications and changes may be made therein. Therefore, the present disclosure will be described in detail with reference to particular embodiments shown in the accompanying drawings. However, it should be understood that there is no intent to limit various embodiments of the present disclosure to the particular embodiments disclosed, but the present disclosure should be construed to cover all modifications, equivalents, and alternatives falling within the ambit of the various embodiments of disclosure. In the description of the drawings, identical or similar reference numerals are used to designate identical or similar elements.

As used in various embodiments of the present disclosure, the expressions "include", "may include" and other conjugates refer to the existence of a corresponding disclosed function, operation, or constituent element, and do not limit one or more additional functions, operations, or constituent elements. Further, as used in various embodiments of the present disclosure, the terms "include", "have" and their conjugates may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

Further, as used in various embodiments of the present disclosure, the expression "or" includes any or all combinations of words enumerated together. For example, the expression "A or B" may include A, may include B, or may include both A and B.

While expressions including ordinal numbers, such as "first" and "second", as used in various embodiments of the present disclosure may modify various constituent elements, such constituent elements are not limited by the above expressions. For example, the above expressions do not limit the sequence and/or importance of the corresponding elements. The expressions may be used to distinguish a component element from another component element. For example, a first user device and a second user device indicate different user devices although both of them are user devices. For example, a first constituent element may be termed a second constituent element, and likewise a second constituent element may also be termed a first constituent element without departing from the scope of various embodiments of the present disclosure.

It should be noted that if it is described that one component element is "coupled" or "connected" to another component element, the first component element may be directly coupled or connected to the second component, and a third component element may be "coupled" or "connected" between the first and second component elements. Conversely, when one component element is "directly coupled' or "directly connected" to another component element, it may be construed that a third component element does not exist between the first component element and the second component element.

The terms as used in various embodiments of the present disclosure are merely for the purpose of describing particular embodiments and are not intended to limit the various embodiments of the present disclosure. As used herein, the singular forms are intended to include the plural forms as well, unless the context clearly indicates otherwise.

Unless defined otherwise, all terms used herein, including technical terms and scientific terms, have the same meaning as commonly understood by a person of ordinary skill in the art to which various embodiments of the present disclosure pertain. Such terms as those defined in a generally used dictionary are to be interpreted to have the meanings equal to the contextual meanings in the relevant field of art, and are not to be interpreted to have ideal or excessively formal meanings unless clearly defined in various embodiments of the present disclosure.

An electronic device according to various embodiments of the present disclosure may be a device having a function provided through colors emitted according to states of an electronic device or a function of detecting a gesture or detecting a signal from a living body. For example, the electronic device may include at least one of a smart phone, a tablet personal computer (PC), a mobile phone, a video phone, an e-book reader, a desktop PC, a laptop PC, a netbook computer, a personal digital assistant (PDA), a portable multimedia player (PMP), an MP3 player, a mobile medical device, a camera, a wearable device (e.g., a head-mounted-device (HMD) such as electronic glasses, electronic clothes, an electronic bracelet, an electronic necklace, an electronic appcessory, an electronic tattoo, or a smart watch).

According to an embodiment of the present disclosure, the electronic device may be a smart home appliance having a function of a display lamp emitting various colors or a function of detecting a gesture or a living body signal. The smart home appliances may include at least one of, for example, televisions, digital video disk (DVD) players, audio players, refrigerators, air conditioners, cleaners, ovens, microwaves, washing machines, air purifiers, set-top boxes, TV boxes (e.g., HomeSync™ of Samsung, Apple TV™, or Google TV™), game consoles, electronic dictionaries, electronic keys, camcorders, or electronic frames.

According to some embodiments, the electronic device may include at least one of various medical appliances (e.g., magnetic resonance angiography (MRA), magnetic resonance imaging (MRI), computed tomography (CT), and ultrasonic machines), navigation equipment, a global positioning system (GPS) receiver, an event data recorder (EDR), a flight data recorder (FDR), automotive infotainment device, electronic equipment for ships (e.g., ship navigation equipment and a gyrocompass), avionics, security equipment, a vehicle head unit, an industrial or home robot, an automatic teller machine (ATM) of a banking system, and a point of sales (POS) of a shop.

According to some embodiments of the present disclosure, the electronic device may include at least one of a furniture element, a part of a building/structure, an electronic board, an electronic signature receiving device, a projector, and various measuring devices (for example, water supply, electricity, gas, and electric wave measuring devices), which have a function provided through colors emitted according to states of an electronic device or a function of detecting a gesture or a body signal. The electronic device according to various embodiments of the present disclosure may be a combination of one or more of the aforementioned various devices. Further, the electronic device according to various embodiments of the present disclosure may be a flexible device. Further, it will be apparent to those skilled in the art that the electronic device according to various embodiments of the present disclosure is not limited to the aforementioned devices.

Hereinafter, the electronic device according to the various embodiments will be described with reference to the accompanying drawings. The term "user" used in the various embodiments may refer to a person or a device (e.g., an artificial intelligence electronic device) using the electronic device.

FIG. 1 illustrates a network environment including an electronic device according to various embodiments of the present disclosure. Referring to FIG. 1, an electronic device 101 may include a bus 110, a processor 120, a memory 130, an input/output interface 140, a display 150, a communication interface 160, and a variable detection module 170.

The bus 110 may be a circuit that interconnects the above-described elements and delivers communications (for example, a control message) between the above-described elements.

The processor 120 may receive a command from other components (for example, the memory 130, the input/output interface 140, the display 150, the communication interface 160, or the variable detection module 170) through the bus 110, analyze the received command, and perform calculation or data processing according to the analyzed command.

The memory 130 may store instructions or data received from the processor 120 or other elements (for example, the input/output interface 140, the display 150, the communication interface 160, the variable detection module 170, or the like) or generated by the processor 120 or other elements. The memory 130 may include programming modules such as, for example, a kernel 131, middleware 132, an Application Programming Interface (API) 133, or an application 134. Each of the programming modules described above may be formed of software, firmware, and hardware, or a combination thereof.

The kernel 131 may control or manage system resources (for example, the bus 110, the processor 120, the memory 130, and the like) used to perform operations or functions implemented in the remaining programming modules, for example, the middleware 132, the API 133, and the applications 134. Furthermore, the kernel 131 may provide an interface through which the middleware 132, the API 133, and the application 134 may access individual component elements of the electronic device 101 to control or manage them.

The middleware 132 may serve as an intermediary such that the API 133 or the application 134 communicates with the kernel 131 to transmit/receive data. Further, in relation to requests for operation received from the applications 134, the middleware 132 may control (for example, scheduling or load-balancing) the requests by using, for example, a method of determining a sequence for using system resources (for example, the bus 110, the processor 120, the memory 130, or the like) of the electronic device 101 with respect to at least one application among the applications 134.

The API 133 is an interface by which the applications 134 control functions provided from the kernel 131 or the middleware 132, and may include, for example, at least one interface or function (for example, instructions) for file control, window control, image processing, text control, or the like.

According to the various embodiments of the present disclosure, the applications 134 may include a Short Message Service (SMS)/Multimedia Message Service (MMS) application, an e-mail application, a calendar application, an alarm application, a health care application (for example, an application for measuring a work rate or a blood sugar), an environment information application (for example, an application for providing atmospheric pressure, humidity, or temperature information). Additionally or alternately, the application 134 may an application related to an information exchange between the electronic device 101 and an external electronic device (for example, an electronic device 104). The application related to the information exchange may include, for example, a notification relay application for transmitting specific information to the external electronic device, or a device management application for managing the external electronic device.

For example, the notification relay application may include a function of transferring notification information generated in other applications (for example, the SMS/MMS application, the e-mail application, the health care application, or the environmental information application) of the electronic device 101 to external electronic devices (for example, the electronic device 104). Additionally or alternatively, the notification relay application may receive notification information from, for example, external electronic devices (for example, the electronic device 104) and provide the same to a user. The device management application may manage (for example, install, delete, or update), for example, at least some functions (for example, turning external electronic device (or some elements) on or off, or adjusting the brightness (or resolution) of a display) of external electronic device (for example, the electronic device 104) that communicates with the electronic device 101, applications performed in the external electronic device, or services (for example, a phone call service, or a messaging service) provided in the external electronic device.

According to various embodiments, the application 134 may include applications, which are designated according to the property (for example, the type of electronic device) of the external electronic device (for example, the electronic device 104). For example, in a case where the external electronic device is an MP3 player, the applications 134 may include an application related to the reproduction of music. Similarly, when the external electronic device is a mobile medical device, the application 134 may include an application related to health care. According to an embodiment of the present disclosure, the application 134 may include at least one of applications designated in the electronic device 101 or applications received from an external electronic device (for example, a server 106 or the electronic device 104).

The input/output interface 140 may transmit a command or data input from the user through an input/output device (for example, sensor, keyboard, or touch screen) to the processor 120, the memory 130, the communication interface 160, or the variable detection module 170 through, for example, the bus 110. For example, the input/output interface 140 may provide, to the processor 120, data for a user's touch which is input through the touch screen. Furthermore, through the input/output device (for example, a speaker or a display), the input/output interface 140 may output instructions or data received from the processor 120, the memory 130, the communication interface 160, or the variable detection module 170 through the bus 110. For example, the input/output interface 140 may output voice data processed through the processor 120 to a user through a speaker.

The display 150 may display various pieces of information (for example, multimedia data or text data) to a user.

The communication interface 160 may connect communication between the electronic device 101 and the external electronic device (for example, the electronic device 104 or the server 106). For example, the communication interface 160 may be connected to a network 162 through wireless or wired communication to communicate with the external device. The wireless communication may include at least one of, for example, Wi-Fi, Bluetooth (BT), Near Field Communication (NFC), Global Positioning System (GPS) and cellular communication (for example, Long Term Evolution (LTE), LTE-A, Code Division Multiple Access (CDMA), Wideband CDMA (WCDMA), Universal Mobile Telecommunication System (UMTS), Wireless Broadband (WiBro), Global System for Mobile communication (GSM), and the like the like). The wired communication may include at least one of, for example, a Universal Serial Bus (USB), a High Definition Multimedia Interface (HDMI), Recommended Standard 232 (RS-232), and a Plain Old Telephone Service (POTS).

According to an embodiment, the network 162 may be a communication network. The communication network may include at least one of a computer network, the Internet, the Internet of things, and a telephone network. According to one embodiment, a protocol (for example, a transport lay protocol, data link layer protocol, or a physical layer protocol) for communication between the electronic device 101 and the external device may be supported by at least one of the applications 134, the application programming interface 133, the middleware 132, the kernel 131, and the communication interface 160.

The variable detection module 170 will be described in more detail with reference to FIGS. 2 to 11.

Figure 2A:
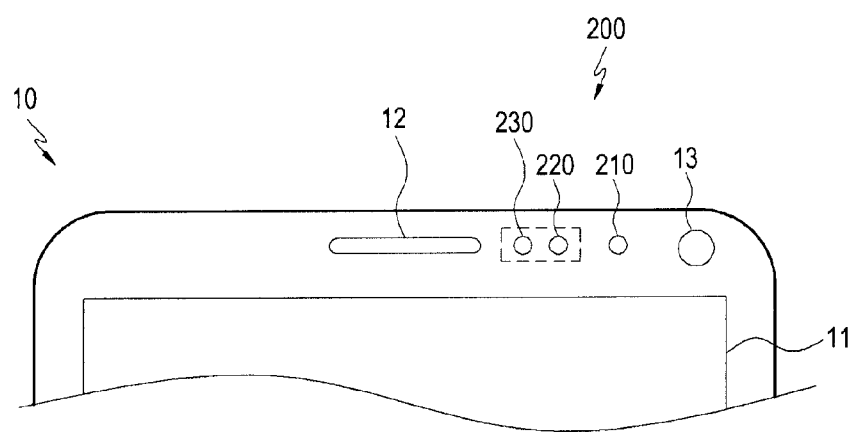
FIG. 2A and FIG. 2B are diagrams illustrating a front surface of an electronic device according to one of various embodiments of the present disclosure.
Figure 2B:
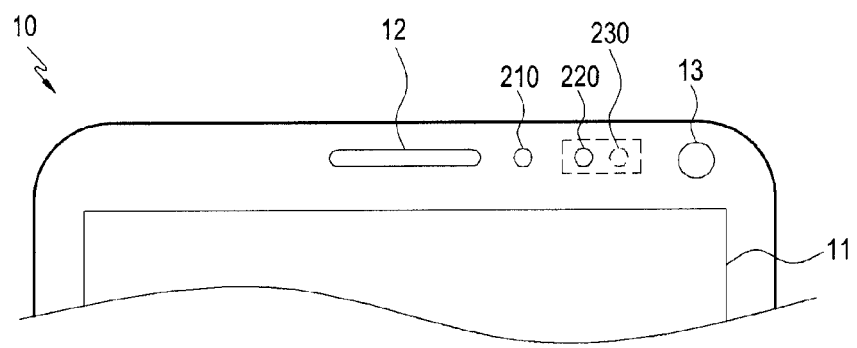
Figure 3:
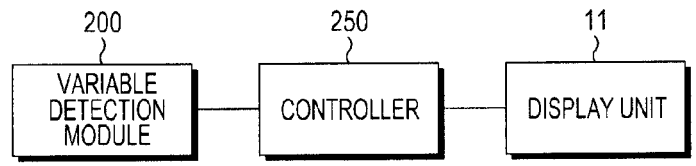
FIG. 3 is a block diagram illustrating an electronic device according to one of various embodiments of the present disclosure.

FIG. 2A and FIG. 2B are diagrams illustrating a front surface of an electronic device 10 according to one of various embodiments of the present disclosure. FIG. 3 is a block diagram illustrating an electronic device according to one of various embodiments of the present disclosure.

Referring to FIGS. 2A, 2B, and 3, the electronic device 10 according to various embodiments of the present disclosure includes a display unit 11 that displays images on a front surface thereof, and may further recognizes user input through a variety of touches and gestures, according to the function and design of the electronic device and/or a respective program. A camera 13, a speaker 12, and a microphone (not illustrated) are provided around the display unit 11.

The electronic device 10 according to an embodiment of the present disclosure may further include a variable detection module 200 and a controller 250. The variable detection module 200 may correspond to the variable detection module 170 of FIG. 1. The variable detection module 200 may be mounted on a periphery of the display unit 11, such as, for example, adjacent to the speaker 12 disposed on the front surface of the electronic device 10. However, it is understood that the variable detection module 200 may be disposed or installed at any suitable location of the electronic device 10.

The variable detection module 200 may include a first light emitting unit 210, a second light emitting unit 220, and a light receiving unit 230. The variable detection module 200 may be implemented such that two different signals may be variably detected, in some cases, according to desired configuration settings of a user of the electronic device.

The first light emitting unit 210, the second light emitting unit 220, and the light receiving unit 230 may be operated separately or together according to, for example, the configuration settings of a user, such that the different signals may be detected variably according to configuration settings. The variable detection module 200 may be configured such that the first light emitting unit 210, the second light emitting unit 220, and the light receiving unit 230 are operated according to separate configuration settings for each sensor, or alternatively the first light emitting unit 210, the second light emitting unit 220, and the light receiving unit 230 are operated utilizing a single configuration setting, such as a first setting or a second setting of the user. Here, the separate configurations may mean that the sensors are individually configured by each separate configuration setting, each setting not influencing the other settings. That is, the first light emitting unit 210 may be operated separately from the second light emitting unit 220 and the light receiving unit 230, and the second light emitting unit 220 and the light receiving unit 230 may be operated as proximity sensors for detecting signals separately from the first light emitting unit 210. Furthermore, another configuration may mean that the configuration settings are operated or applied in association with each other. That is, the first light emitting unit 210, the second light emitting unit 220, and the light receiving unit may be operated as a single sensor for detecting signals, and in another embodiment of the present disclosure, may be utilized as a body detection sensor for detecting body signals.

The variable detection module 200 may be configured such that the first light emitting unit 210, the second light emitting unit 220, and the light receiving unit 230 are separately operated in a first mode "M1" according to configuration settings of the user. For example, the first light emitting unit 210 may emit one or more visible rays of red, green, and blue light, either in a single or complex configuration or manner, thus operating as an LED indicator (thus operating in a notification mode). The second light emitting unit 220 and the light receiving unit 230 may be operated to detect a gesture and/or a motion (thus operating in a gesture and motion sensor mode).

The variable detection module 200 may be configured such that the first light emitting unit 210, the second light emitting unit 220, and the light receiving unit 230 are operated within a single configuration in a second mode "M2" according to configuration settings of the user. For example, the light emitted from the first light emitting unit 210 and the second light emitting unit 220 may be transmitted and received by the light receiving unit 230, allowing the variable detection module 200 to operate as a body signal sensor, including at least one of a heart rate and/or a blood oxygen saturation.

The controller 250 may operate the variable detection module 200 in the first mode M1 or the second mode M2 according to the configuration settings of the user, and may execute one or more functions of the electronic device 10 (such as the display unit 11) according or in response to a signal detected by the variable detection module 200 (thus operating in a biometric sensor mode).

Figure 4:
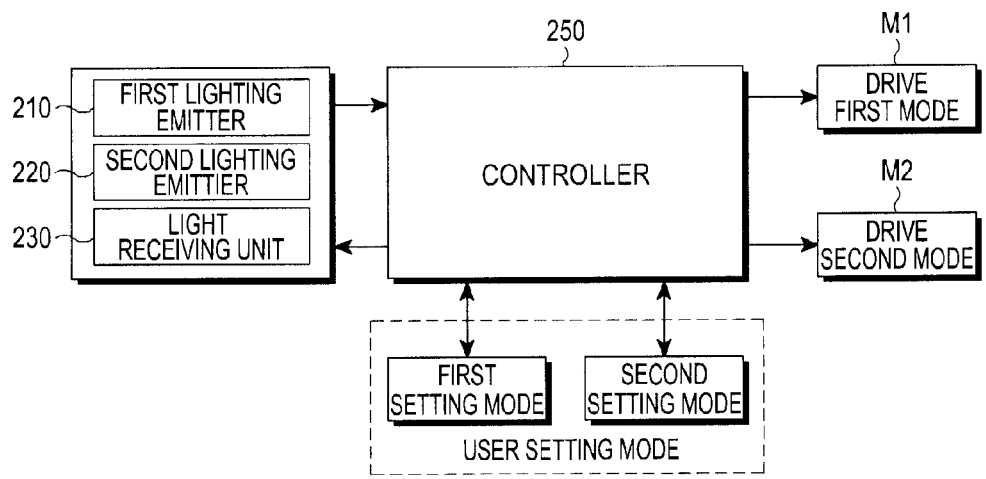
FIG. 4 is a diagram illustrating driving of an electronic device according to one of various embodiments of the present disclosure.

FIG. 3 is a block diagram illustrating operation of an electronic device according to one of various embodiments of the present disclosure. FIG. 4 is a diagram illustrating driving of an electronic device according to one of various embodiments of the present disclosure.

Referring to FIG. 3 and FIG. 4, as described above, the electronic device 10 may detect different signals through a single variable detection module 200. The user may change the setting selecting a mode of the variable detection module 200 through configuration settings indicated by the user. If the user sets the first setting mode or the second setting mode, the controller 250 may operate the variable detection module 200 according to the selected setting mode. For example, if the user selects the first setting mode, the selected value is applied to the controller 250, and the controller 250 may operate the variable detection module 200 such that the variable detection module 200 is driven in the first mode M1. If the user selects the second setting mode, the selected value is applied to the controller 250, and the controller 250 may operate the variable detection module 200 in the second mode M2. When the variable detection module 200 is driven in the first mode M1, the first light emitting unit 210 may be utilized as an LED indicator to display a state of the electronic device 10, and the second light emitting unit 220 and the light receiving unit 230 may be operated as a detection unit to detect motion or proximity of an object. When the variable detection module 200 is driven in the second mode M2, the first light emitting unit 210 and the second light emitting unit 220 may be operated as a aggregated light emitting unit 240, the light emitting unit 220 and the light receiving unit 230 may be operated as a detection unit for detecting a body signal.

The first light emitting unit 210 may include a first light source that emits one or more colors of light, including red, green, and blue light, and may also be referred to as a light emitter. The first light source may itself include a light source that emits colors of red, green, and blue. The first light source may be configured such that light of red, blue, and green may be emitted by a single light module. In another embodiment, the first light source may include disparate light sources that emit light of red, green, and blue light separately from each disparate light source. The first light source may be operated as an LED indicator for displaying a state of the electronic device, and may be operated together with the second light source, which will be described below, to be operated in tandem with the aggregated light emitting unit 240 to detect a body signal.

For example, the first light source may emit one or more visible rays of red, green, and blue light in a single or complex fashion or arrangement according to a configuration setting or state, thus operating to display a state of the electronic device in the first mode M1. For example, the first light source may thus be operated as an LED indicator for displaying a charging state of a battery. A red light source may be utilized to indicate that the battery is being charged, and the green light source may indicate that the battery is completely charged. For example, the first light source may be operated as an LED indicator displaying reception and transmission of communication or information by the electronic device. For example, when a message has arrived at the electronic device 10, and a light-based alarm indicator for the message is desired, the red, green, and/or blue light may be alternately emitted, thus operating as an LED indicator notifying the user of the presence of an unread message. The above-described examples are some examples of operation of an LED indicator that may be set as the first light source in the first mode M1. It is understood that emission of light from the first light source may be arbitrarily changed or modified according to configuration settings of the LED indicator.

The first light source may be operated to emit one of red and/or green light to detect the desired body signal information in the second mode M2. For example, the first light source may emit green light to detect blood oxygen saturation of the user among body information. The first light source may alternatively emit red light to detect a heart rate of the user. For example, if the IR LED having a 80 nm wavelength in the transmitter and the light having a 660 nm wavelength in the RED LED are emitted (or transmitted) simultaneously, the emitted LEDs are reflected by platelets flowing along the bloodstream and received at the photo diode (e.g., receiver), and then biometric information such as heart rate or blood oxygen saturation may be measured based on the average of the speeds at which the emitted LEDs are reflected.

The second light emitting unit 220 may be disposed adjacent to the first light emitting unit 210 and, for example, to the first light source, and may also be referred to as a transmitter. As the second light emitting unit 220 is disposed adjacently to the first light emitting unit 210, the second light emitting unit 220 may emit light of a specific wavelength (e.g., infrared) together with the first light emitting unit 210 in the second mode, allowing detection of a body signal (e.g., biometric information). The second light emitting unit 220 may include a second light source facilitating the emission of the light of the particular wavelength, thus enabling detection of body signals in the second mode M2, and detection of proximity signals in the first mode M1.

The light receiving unit 230 may be mounted adjacently to the second light emitting unit 220. In the first mode (M1), the light receiving unit 230 may receive a signal transmitted from the second light source. In the second mode (M2), the light receiving unit 230 may together receive signal transmitted from the first light source and the second light source. The light receiving unit 230 may include a photo diode, and may also be referred to as a receiver.

The variable detection module 200 may be configured so that the first light source 210, the second light source 220, and the light receiving unit 230 are sequentially mounted, arranged left to right on a front surface of the electronic device 10 (as seen in FIG. 2A). Alternatively, the variable detection module 200 may be configured such that the first light source 210, the second light source 220, and the light receiving unit 230 are sequentially mounted from the right to left of a front surface of the electronic device 10 (as seen in FIG. 2B).

As described above, the controller 250 may operate the variable detection module 200 in the first mode (M1) or the second mode (M2) according to settings of the user, and may control the electronic device 10 according to a detected signal of the variable detection module 200.

Figure 5:
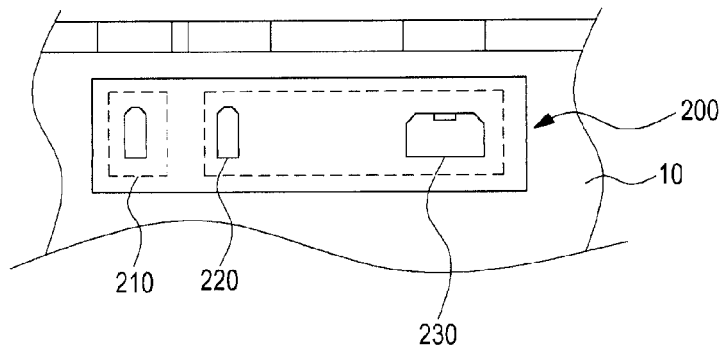
FIG. 5 is a diagram illustrating a state in which an electronic device is driven in a first mode according to one of various embodiments of the present disclosure.
Figure 6:
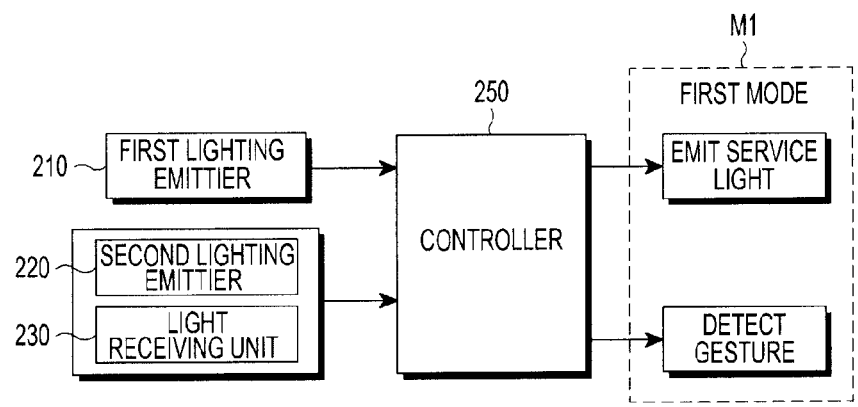
FIG. 6 is a block diagram illustrating a state in which an electronic device is driven in a first mode according to one of various embodiments of the present disclosure.

FIG. 5 is a diagram illustrating a state in which an electronic device is operates a variable detection module in a first mode (M1) according to one of various embodiments of the present disclosure. FIG. 6 is a block diagram illustrating a state in which an electronic device operates the variable detection module in the first mode according to one of various embodiments of the present disclosure.

Referring to FIG. 5 and FIG. 6, if the variable detection module 200 is operated in the first mode (M1) by command of the controller 250, the controller 250 may cause the first light emitting unit 210, the second light emitting unit 220, and the light receiving unit 230 to operate separately. That is, the first light emitting unit 210 operates to emit light as an LED indicator (hereafter, referred to as 'a service light' or 'a service light source') according to desired user configuration settings. Similarly, the second light emitting unit 220 and the light receiving unit 230 are operated as to detect a proximity. Accordingly, the first light emitting unit 210 may alternately emit one or more of red, green, and blue light, allowing the first light emitting unit 210 to operate as an LED indicator indicating a state of the electronic device. The second light emitting unit 220 and the light receiving unit 230 may operate in a sleep mode and a wakeup mode. For example, the second light emitting unit 220 and the light receiving unit 230 may function as proximity sensors, but when a separate signal is not detected, the second light emitting unit 220 and the light receiving unit 230 may execute a sleep mode. If a signal such as a proximity signal or a touch signal is detected by the second light emitting unit 220 and the light receiving unit 230 in the sleep mode, the second light emitting unit 220 and the light receiving unit 230 execute a wakeup mode and function to detected an input signal.

If an object, such as, for example, a cheek of the user, approaches the second light emitting unit 220 and the light receiving unit 230 such that a signal is detected, triggering a wakeup mode, the detected signal may be transmitted to the controller 250. The controller 250 may, according to the first mode M1, cause activation or deactivation of the display unit 11, according to the detected signal.

Figure 7:
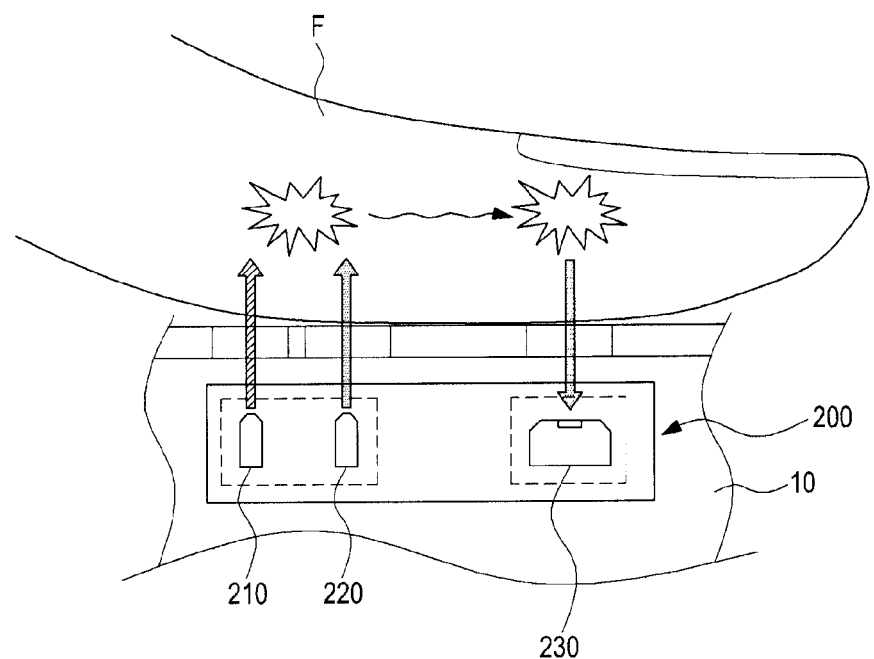
FIG. 7 is a diagram illustrating a state in which an electronic device is driven in a second mode according to one of various embodiments of the present disclosure.
Figure 8:
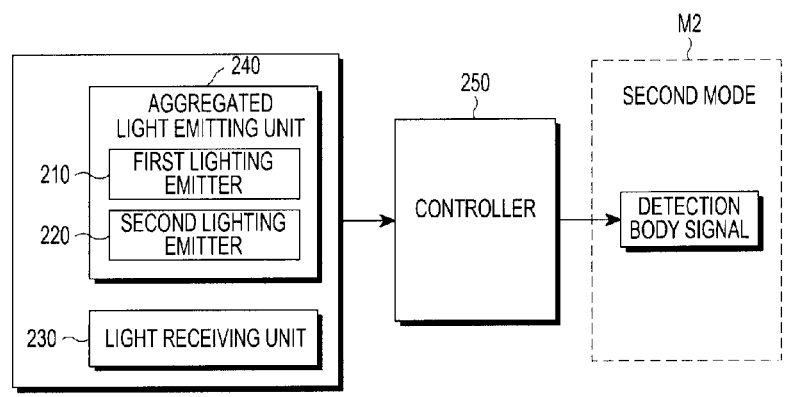
FIG. 8 is a block diagram illustrating a state in which an electronic device is driven in a second mode according to one of various embodiments of the present disclosure.

FIG. 7 is a diagram illustrating a state in which an electronic device operates in a second mode according to one of various embodiments of the present disclosure. FIG. 8 is a block diagram illustrating a state in which an electronic operates in the second mode according to one of various embodiments of the present disclosure.

Referring to FIGS. 7 and 8, if the controller 250 causes the variable detection module 200 to operate in the second mode M2 (per a configuration setting of the user), the controller 250 cause the first light emitting unit 210, the second light emitting unit 220, and the light receiving unit 230 to operate together as a single detection unit for detecting a body signal. That is, in the second mode M2, the variable detection module 200 may be operated such that an aggregated light emitting unit 240 including the first light emitter 210 and the second light emitter 220 to function as a single transmission unit. The light receiving unit 230 may then operate to receive a signal transmitted from the aggregated light emitting unit 240. Accordingly, the aggregated light emitting unit 240 and the light receiving unit 230 may detect a body signal of the user. If the variable detection module 200 operates in the second mode M2, the first light emitter 210 (e.g. first light source) and the second light emitter 220 (e.g., second light source) operate in tandem as the aggregated light emitting unit 240, and the light receiving unit 230 operates to receive a light transmission from the aggregated light emitting unit 240. If a finger of the user is disposed on the aggregated light emitting unit 240 and the light receiving unit 230, the first light emitter of the aggregated light emitting unit 240 may emit one visible ray of red and/or green light, and the second light source may emit an infrared ray. Depending on a body signal to be detected, the first light source may emit one of a visible ray of red or green light, and the second light source in both cases may emit an infrared ray. The light receiving unit 230 may receive the signal emitted from the aggregated light emitting unit 240, the light transmission having passed through the body of the user. For example, if the IR LED having a 80 nm wavelength in the transmitter and the light having a 660 nm wavelength in the RED LED are emitted (or transmitted) simultaneously, the emitted LEDs are reflected by platelets flowing along the bloodstream and received at the photo diode (e.g., receiver), and then biometric information such as heart rate or blood oxygen saturation may be measured based on the average of the speeds at which the emitted LEDs are reflected. The controller 250 may then display the user's body information on the display unit 11, according to the signals detected by operation of the aggregated light emitting unit 240, and the light receiving unit 230.

An operational process of the above-configured electronic device 10 will be described with reference to FIGS. 9 to 11.

Figure 9:
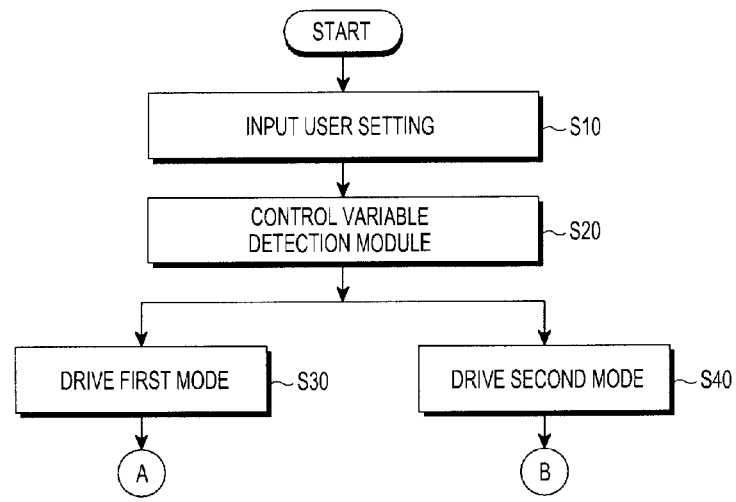
FIG. 9 is a flowchart illustrating driving of an electronic device according to one of various embodiments of the present disclosure.

FIG. 9 is a flowchart illustrating operation of an electronic device according to one of various embodiments of the present disclosure.

Referring to FIG. 9, an operation mode of the variable detection module 200 may be altered by a user setting, as received by the electronic device (S10). In accordance with the user settings, the controller may operate the variable detection module 200 in the first mode or the second mode (S20). That is, the variable detection module 200 may operate in a first mode including a notification mode, where light emissions of an LED indicator indicate a state of the electronic device, a gesture and motion sensor mode for detecting gestures or motion or proximity, and a biometric sensor mode where a body signal is detected. In addition, as long as the electronic device 10 is operable and supplied with power, the variable detection module 200 may be set to be operate at least one of the two modes (S30 and S40).

For example, because it is not necessary for the user to detect body signals at all times, the variable detection module 200 may be set to operate in the first mode M1 as a default or general setting, that is, in common use for the electronic device, in which it is usually unnecessary to detect a body signal.

Figure 10:
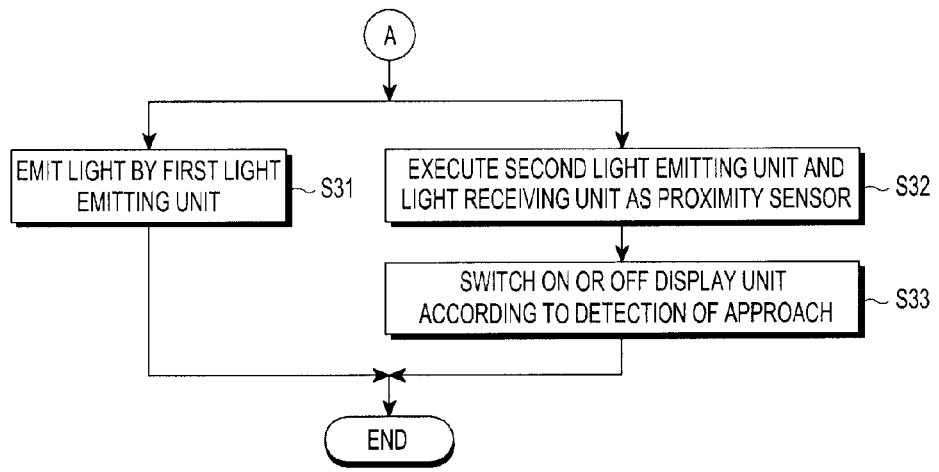
FIG. 10 is a flowchart illustrating driving of a first mode of a variable detection module in an electronic device according to one of various embodiments of the present disclosure.

FIG. 10 is a flowchart illustrating operation of a first mode of a variable detection module in an electronic device according to one of various embodiments of the present disclosure.

Referring to FIG. 10, if the variable detection module 200 is set to operate in the first mode M1 in the electronic device 10, the first light emitting unit 210 may visually display to the user with a state or in-use state of the electronic device 10 (S31). The second light emitting unit 220 and the light receiving unit 230 may operate as a proximity sensor for detecting a gesture (S32). Accordingly, when the battery is being charged or completely charged, the first light emitting unit 210 may emit colored light (e.g., red and green) according to a user setting. When a call is received by the electronic device 10, the first light emitting unit 210 may repeatedly emit light of red, green, and/or blue, according to a user setting. When a phone call is executed on the electronic device 10, a cheek of the user may be disposed close to or adjacent to the front surface of the electronic device 10, such that the second light emitting unit 220 and the light receiving unit 230 detect the cheek of the user.

A signal detected by the second light emitting unit 220 and the light receiving unit 230 may receive and processed by the controller 250 to execute a function. For example, the controller 250 may cause a power for the display unit 11 to activate or deactivate (S33). Accordingly, the electronic device 10 can reduce power consumption by disabling the display unit 11 when it is detected that the device 10 is not being actively used.

It is understood that the present disclosure is not limited to the embodiments described above. For example, a setting value may be arbitrarily changed, for example, thus causing a user interface to be executed and displayed on the display unit 11 in response to detection of a signal indicating proximity or a gesture by the second light emitting unit 220 and/or the light receiving unit 230. Any function so desired may be executed.

Figure 11:
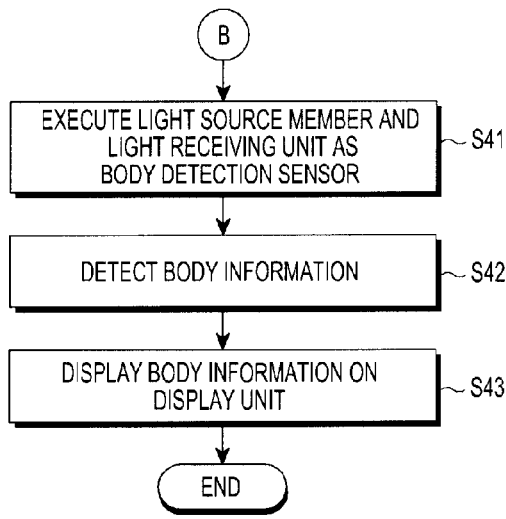
FIG. 11 is a flowchart illustrating driving of a second mode of a variable detection module in an electronic device according to one of various embodiments of the present disclosure.

FIG. 11 is a flowchart illustrating operation of a second mode of a variable detection module in an electronic device according to one of various embodiments of the present disclosure.

Referring to FIG. 11, if the variable detection module 200 is set to operate in the second mode M2, the first light emitting unit 210 and the second light emitting unit 220 may operate as a single light emitting unit 240, and the light receiving unit 230 may operate to receive signals transmitted from the aggregated light emitting unit 240, so that the aggregated light emitting unit 240 and the light receiving unit 230 operate as body detection sensors (S41).

If an object, such as, for example, a finger of the user is disposed on the aggregated light emitting unit 240 and the light receiving unit 230 (that is, the light emitting unit 240, in detail), the first light source and the second light source may emit visible rays of red and/or green light and an infrared ray. The visible rays and the infrared ray emitted from the first light source and the second light source may be emitted through the finger of the user disposed on the light emitting unit 240, and the light receiving unit 230 may receive light reflected by platelets of the user. Accordingly, the detected light may be received through the light receiving unit 230 (S42). The controller 250 may process the information and display the results including the body information of the user on the display unit 11 (S43). For example, if the IR LED having a 80 nm wavelength in the transmitter and the light having a 660 nm wavelength in the RED LED are emitted (or transmitted) simultaneously, the emitted LEDs are reflected by platelets flowing along the bloodstream and received at the photo diode (e.g., receiver), and then biometric information such as heart rate or blood oxygen saturation may be measured based on the average of the speeds at which the emitted LEDs are reflected. Accordingly, the user may review information such as a heart rates or blood oxygen saturation through the display unit 11.

As described above, the variable detection sensor may detect two different signals, via the first light emitting unit 210, the second light emitting unit 220, and the light receiving unit 230. That is, the first light emitting unit 210, the second light emitting unit 220, and the light receiving unit 230 may be operated in the first mode M1, allowing utilization of the LED indicator to generate notifications, and detection of proximity and/or gestures by the light receive unit 230. The same may be operated in the second mode M2, allowing utilization of the first light emitting unit 210, the second light emitting unit 220, and the light receiving unit 230 to detect biometric information of a user.

Figure 12:
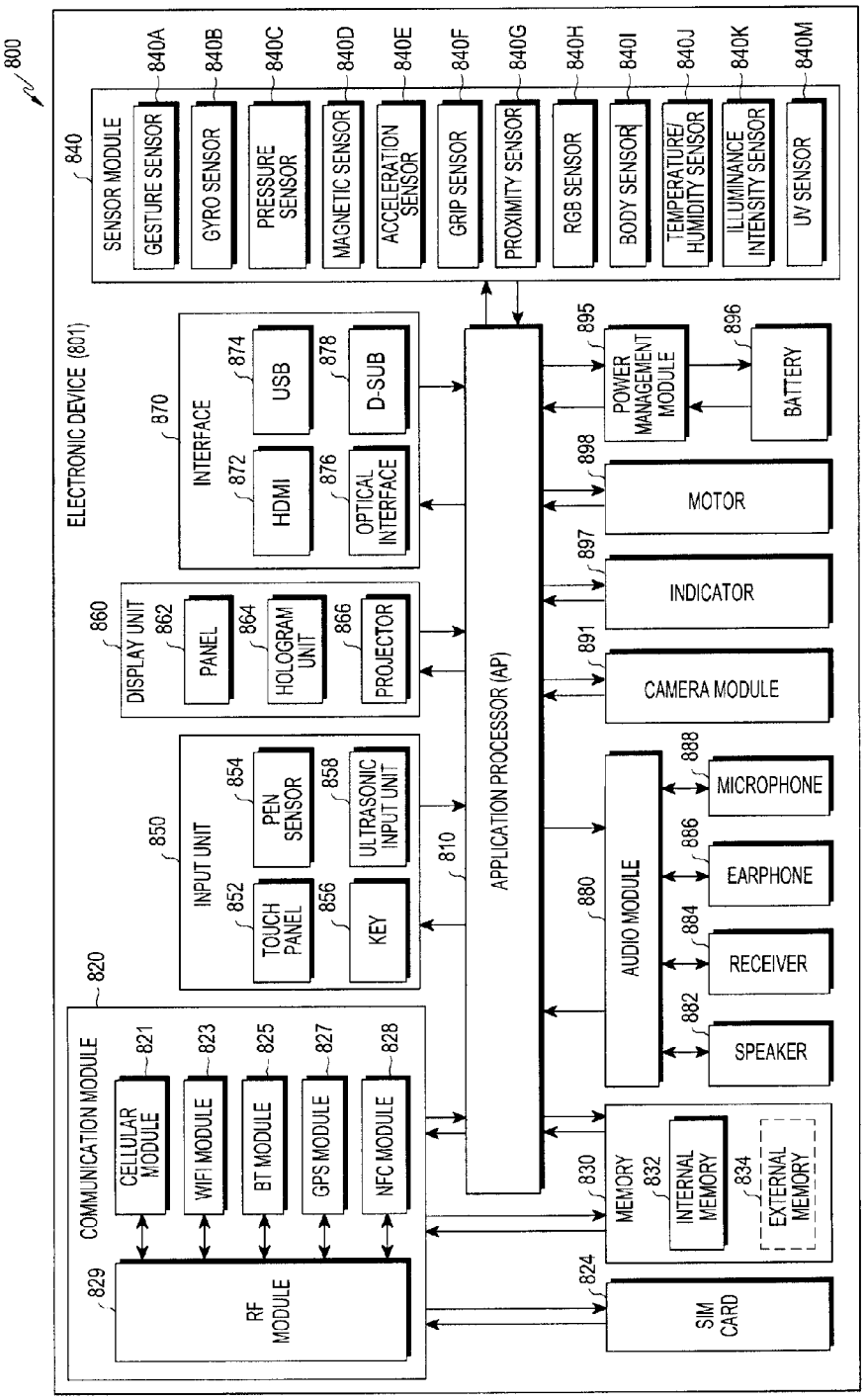
FIG. 12 is a block diagram of an electronic device according to various embodiments of the present disclosure.

FIG. 12 illustrates a block diagram 800 of an electronic device 801 according to various embodiments of the present disclosure. The electronic device 801 may constitute, for example, all or part of the electronic device 101 illustrated in FIG. 1. Referring to FIG. 12, the electronic device may include at least one application processor 810, a communication module 820, a Subscriber Identification Module (SIM) card 824, a memory 830, a sensor module 840, an input unit 850, a display unit 860, an interface 870, an audio module 880, a camera module 891, a power management module 895, a battery 896, an indicator 897, and a motor 898.

The AP 810 may control a plurality of hardware or software components connected to the AP 810 by driving an operating system or an application program, process various data including multimedia data, and perform calculations. The AP 810 may be embodied as, for example, a System on Chip (SoC). According to an embodiment, the AP 810 may further include a graphic processing unit (GPU) (not illustrated).

The communication module 820 (for example, the communication interface 160) may perform data transmission/reception in communication between the electronic device 801 (for example, the electronic device 101) and other electronic devices (for example, the electronic device 104 and the server 106) connected thereto through a network. According to an embodiment, the communication module 820 may include a cellular module 821, a WiFi module 823, a BlueTooth (BT) module 825, a Global Positioning System (GPS) module 827, a Near Field Communication (NFC) module 828, and a Radio Frequency (RF) module 829.

The cellular module 821 may provide a voice call, a video call, an SMS service, an Internet service, and the like through a communication network (for example, LTE, LTE-A, CDMA, WCDMA, UMTS, WiBro, or GSM). Also, the cellular module 821 may identify and authenticate an electronic device in a communication network by using, for example, a subscriber identification module (for example, the SIM card 824). According to an embodiment, the cellular module 821 may perform at least some functions that may be provided by the AP 810. For example, the cellular module 821 may perform at least a part of a multimedia control function.

According to an embodiment, the cellular module 821 may include a communication processor (CP). Further, the cellular module 821 may be implemented by, for example, an SoC. Although FIG. 12 illustrates that the components such as the cellular module 821 (for example, communication processor), the memory 830, and the power managing module 895 are separate components of the AP 810, the AP 810 may include at least some of the above described components (for example, cellular module 821) according to an embodiment.

According to an embodiment, the AP 810 or the cellular module 821 may load a command or data received from at least one of a non-volatile memory and other elements connected thereto into a volatile memory and process the loaded command. Further, the AP 810 or the cellular module 821 may store data received from or generated by at least one of the other components in a non-volatile memory.

Each of the WiFi module 823, the BT module 825, the GPS module 827, and the NFC module 828 may include, for example, a processor for processing data transmitted/received through the corresponding module. Although each of the cellular module 821, the WiFi module 823, the BT module 825, the GPS module 827, and the NFC module 828 are illustrated as separate blocks in FIG. 12, at least some (for example, two or more) of the cellular module 821, the WiFi module 823, the BT module 825, the GPS module 827, and the NFC module 828 may be included in one integrated chip (IC) or IC package according to an embodiment. For example, at least some of processors corresponding to the cellular module 821, the WiFi module 823, the BT module 825, the GPS module 827, and the NFC module 828 respectively (for example, a CP corresponding to the cellular module 821 and a WiFi processor corresponding to the WiFi module 823) may be implemented as one SoC.

The RF module 829 may transmit/receive data, for example, an RF signal. Although not illustrated, the RF module 829 may include, for example, a transceiver, a Power Amp Module (PAM), a frequency filter, a Low Noise Amplifier (LNA) or the like. Further, the RF module 829 may further include a component for transmitting/receiving electronic waves over free air space in wireless communication, for example, a conductor, a conducting wire or the like. Although FIG. 12 shows that the cellular module 821, the WiFi module 823, the BT module 825, the GPS module 827, and the NFC module 828 share one RF module 829, at least one of the cellular module 821, the WiFi module 823, the BT module 825, the GPS module 827, and the NFC module 828 may perform RF signal transmission/reception through a separate RF module.

The SIM card 824 may be a card including a subscriber identification module, and may be inserted into a slot formed in a particular portion of the electronic device. The SIM card 824 may include unique identification information (for example, an integrated circuit card identifier (ICCID)) or subscriber information (for example, an international mobile subscriber identity (IMSI)).

The memory 830 (for example, the memory 130) may include an embedded memory 832 or an external memory 834. The internal memory 832 may include at least one of a volatile memory (for example, a Dynamic Random Access Memory (DRAM), a Static RAM (SRAM), a Synchronous Dynamic RAM (SDRAM), and the like) and a non-volatile memory (for example, a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, and the like).

According to one embodiment, the internal memory 832 may be a solid state drive (SSD). The external memory 834 may further include a flash drive, for example, a Compact Flash (CF), a Secure Digital (SD), a Micro Secure Digital (Micro-SD), a Mini Secure Digital (Mini-SD), an extreme Digital (xD), a memory stick or the like. The external memory 834 may be functionally connected to the electronic device 801 through various interfaces. According to an embodiment, the electronic device 801 may further include a storage device (or storage medium) such as a hard drive.

The sensor module 840 may measure a physical quantity or detect an operation state of the electronic device 801, and may convert the measured or detected information to an electronic signal. The sensor module 840 may include, for example, at least one of a gesture sensor 840A, a gyro sensor 840B, an atmospheric pressure sensor 840C, a magnetic sensor 840D, an acceleration sensor 840E, a grip sensor 840F, a proximity sensor 840G, a color sensor 840H (for example, red, green, and blue (RGB) sensor), a biometric sensor 840I, a temperature/humidity sensor 840J, an illumination sensor 840K, and an Ultra Violet (UV) sensor 840M. Additionally or alternatively, the sensor module 840 may include, for example, an E-nose sensor (not illustrated), an electromyography (EMG) sensor (not illustrated), an electroencephalogram (EEG) sensor (not illustrated), an electrocardiogram (ECG) sensor (not illustrated), an Infrared (IR) sensor, an iris sensor (not illustrated), a fingerprint sensor, and the like. The sensor module 840 may further include a control circuit for controlling one or more sensors included therein.

The input device 850 may include a touch panel 852, a (digital) pen sensor 854, a key 856, or an ultrasonic input device 858. The touch panel 852 may recognize a touch input through at least one of, for example, a capacitive scheme, a resistive scheme, an infrared scheme, and an ultrasonic scheme. The touch panel 852 may further include a control circuit. The capacitive scheme touch panel may recognize physical contact or proximity. The touch panel 852 may further include a tactile layer. In this case, the touch panel 852 may provide a tactile reaction to a user.

The (digital) pen sensor 854 may be embodied, for example, using a method identical or similar to a method of receiving a touch input of a user, or using a separate recognition sheet. The key 856 may include, for example, a physical button, an optical key, or a keypad. The ultrasonic input unit 858 is a unit that can identify data by generating an ultrasonic signal through an input tool (for example, pen) and detecting a sonic wave through a microphone (for example, microphone 888) in the electronic device 801, and is capable of wireless recognition. According to an embodiment, the electronic device 801 may also receive a user input from an external device (for example, computer or server) connected thereto by using the communication module 820.

The display 860 (for example, display 150) may include a panel 862, a hologram device 864, or a projector 866. The panel 862 may be, for example, a Liquid Crystal Display (LCD), Active-Matrix Organic Light Emitting Diode (AM-OLED), or the like. The panel 862 may be embodied to be, for example, flexible, transparent, or wearable. The panel 862 may be also configured as one module together with the touch panel 852. The hologram device 864 may show a stereoscopic image in the air using interference of light. The projector 866 may project light onto a screen to display an image. For example, the screen may be located inside or outside the electronic device 801. According to an embodiment, the display 860 may further include a control circuit for controlling the panel 862, the hologram device 864, or the projector 866.

The interface 870 may include, for example, a High-Definition Multimedia Interface (HDMI) 872, a Universal Serial Bus (USB) 874, an optical interface 876, or a D-sub-miniature (D-sub) 878. The interface 870 may be included in, for example, the communication interface 160 illustrated in FIG. 1. Additionally or alternatively, the interface 870 may include, for example, a Mobile High-definition Link (MHL) interface, a Secure Digital (SD) card/Multi-Media Card (MMC) interface, or an Infrared Data Association (IrDA) standard interface.

The audio module 880 may bidirectionally convert a sound and an electronic signal. At least some components of the audio module 880 may be included in, for example, the input/output interface 140 illustrated in FIG. 1. The audio module 880 may process voice information input or output through, for example, a speaker 882, a receiver 884, earphones 886, the microphone 888 or the like.

The camera module 891 is a device that can take still and moving images, and according to an embodiment, may include one or more image sensors (for example, a front sensor or a rear sensor, not illustrated), a lens (not illustrated), an image signal processor (ISP) (not illustrated), or a flash (for example, an LED or a xenon lamp, not illustrated).

The power management module 895 may manage power of the electronic device 801. Although not illustrated, the power management module 895 may include, for example, a Power Management Integrated Circuit (PMIC), a charger Integrated Circuit (IC), or a battery or fuel gauge.

The PMIC may be mounted to, for example, an integrated circuit or an SoC semiconductor. Charging methods may be classified into a wired charging method and a wireless charging method. The charger IC may charge a battery and prevent over voltage or over current from being flowed from a charger. According to an embodiment, the charger IC may include a charger IC for at least one of the wired charging and the wireless charging. A magnetic resonance scheme, a magnetic induction scheme, or an electromagnetic scheme may be exemplified as the wireless charging method, and an additional circuit for wireless charging, such as a coil loop circuit, a resonance circuit, a rectifier circuit, and the like may be added.

The battery fuel gauge may measure, for example, the remaining amount of battery, a charging voltage and current, or temperature. The battery 896 may store or generate electricity, and may supply power to the electronic device 801 using the stored or generated electricity. The battery 896 may include, for example, a rechargeable battery or a solar battery.

The indicator 897 may show particular statuses of the electronic device 801 or a part (for example, AP 810) of the electronic device 801, for example, a booting status, a message status, a charging status and the like. The motor 898 may convert an electrical signal into a mechanical vibration. Although not illustrated, the electronic device 801 may include a processing unit (for example, GPU) for supporting a mobile TV function. The processing unit for supporting the mobile TV may process media data according to a standard of Digital Multimedia Broadcasting (DMB), Digital Video Broadcasting (DVB), media flow or the like.

Each of the above described elements of the electronic device according to various embodiments of the present disclosure may be formed of one or more components, and the name of a corresponding element may vary according to the type of an electronic device. The electronic device according to various embodiments of the present disclosure may be formed to include at least one of the above described components, and some of the components may be omitted or additional components may be further included. Further, some of the elements of the electronic device according to various embodiments of the present disclosure may be coupled to form a single entity while performing the same functions as those of the corresponding elements before the coupling.

Figure 13:
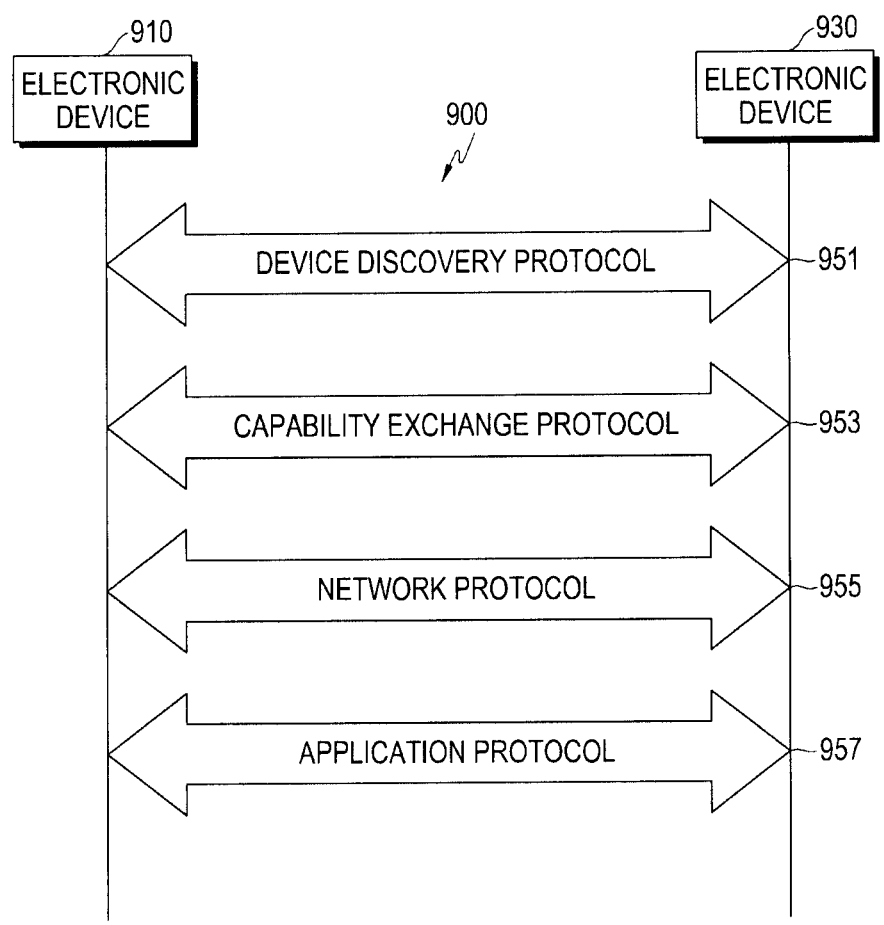
FIG. 13 illustrates communication protocols between a plurality of electronic devices according to various embodiments of the present disclosure.

FIG. 13 illustrates a communication protocol 900 between a plurality of electronic devices (for example, the electronic device 910 and the electronic device 930) according to various embodiments of the present disclosure. Referring to FIG. 13, for example, the communication protocol 900 may include a device discovery protocol 951, a capability exchange protocol 953, a network protocol 955, and an application protocol 957.

According to an embodiment, the device discovery protocol 951 may be a protocol that allows electronic devices (for example, the electronic device 910 or the electronic device 930) to detect an external electronic device that may directly communicate with the electronic devices or that allows the electronic device to be connected to the detected external device. For example, the electronic device 910 (for example, the electronic device 101) may detect the electronic device 930 (for example, the electronic device 104) with a device that may communicate with the electronic device 910 through a communication method (for example, WiFi, BT or a USB) that may be used in the electronic device, using the device discovery protocol 951. For a communication connection with the electronic device 930, the electronic device 910 may acquire identification information of the electronic device 930 detected through the device discovery protocol 951 and store the acquired identification information. For example, the electronic device 910 may establish the communication connection with the electronic device 930 using at least the identification information.

According to an embodiment, the device discovery protocol 951 may be a protocol for mutual authentication among a plurality of electronic devices. For example, the electronic device 910 may perform an authentication between the electronic device 910 and the electronic device 930 based on communication information (for example, a Media Access Control (MAC) address, a Universally Unique IDentifier (UUID), a SubSystem IDentification (SSID), and an Information Provider (IP) address) for the connection with the electronic device 930.

According to an embodiment, the capability exchange protocol 953 may be a protocol for exchanging information related to a service function which is supported by at least one of the electronic device 910 and the electronic device 930. For example, the electronic device 910 or the electronic device 930 may exchange information related to a service function currently provided by each of the electronic device 1010 and the electronic device 1030 through the capability exchange protocol 953. The exchangeable information may include identification information indicating a particular service among a plurality of services which can be supported by the electronic device 910 or the electronic device 930. For example, the electronic device 910 may receive, from the electronic device 930, identification information of a particular service provided by the electronic device 930 through the capability exchange protocol 953. In this case, the electronic device 910 may determine whether the particular service can be supported by the electronic device 910 itself based on the received identification information.

According to an embodiment, the network protocol 955 may be a protocol for controlling flows of data that are transmitted or received to provide, for example, a service between the electronic devices (for example, the electronic device 910 and the electronic device 930) connected to each other for communications. For example, at least one of the electronic device 910 and the electronic device 930 may control errors or data quality using the data/session protocol 955. Additionally or alternatively, the network protocol 955 may determine a transmission format of the data transmitted or received between the electronic device 910 and the electronic device 930. At least one of the electronic device 910 and the electronic device 930 may manage at least one session (for example, connect or complete the session) for exchanging data using the network protocol 955.

According to an embodiment, the application protocol 957 may be a protocol for providing a process or information for exchanging data related to a service provided to an external electronic device. For example, the electronic device 910 (for example, the electronic device 101) may provide the electronic device 930 (for example, the electronic device 104 or the server 106) with a service through the application protocol 957.

According to an embodiment, the communication protocol 900 may include a standard communication protocol, a communication protocol designated by an individual or organization (for example, a communication protocol self-designated by a communication device manufacturing company or a network supplying company) or a combination thereof.

The "module" used in various embodiments of the present disclosure may refer to, for example, a "unit' including one of hardware, software, and firmware, or a combination of two or more of the hardware, software, and firmware. The "module" may be interchangeable with a term, such as a unit, a logic, a logical block, a component, or a circuit. The "module' may be a minimum unit of an integrated component element or a part thereof. The "module" may be a minimum unit for performing one or more functions or a part thereof. The "module" may be mechanically or electronically implemented. For example, the "module" according to various embodiments of the present disclosure may include at least one of an application-specific integrated circuit (ASIC) chip, a field-programmable gate array (FPGA), and a programmable-logic device for performing certain operations, which are now known or will be developed in the future.

At least some of the devices (e.g., modules or functions thereof) or methods (e.g., operations) according to various embodiments of the present disclosure may be implemented by, for example, by a command stored in a computer-readable storage medium in the form of a programming module. When the instruction is performed by at least one processor (for example, the application processor 810), the at least one processor may perform a function corresponding to the instruction. The computer-readable storage medium may be, for example, the memory 830. At least some of the programming modules may be implemented (for example, executed) by, for example, the application processor 810. At least a part of the programming module may include, for example, a module, a program, a routine, a set of instructions and/or a process for performing one or more functions.

The computer readable recording medium may include magnetic media such as a hard disc, a floppy disc, and a magnetic tape, optical media such as a compact disc read only memory (CD-ROM) and a digital versatile disc (DVD), magneto-optical media such as a floptical disk, and hardware devices specifically configured to store and execute program commands, such as a read only memory (ROM), a random access memory (RAM), and a flash memory. In addition, the program instructions may include high class language codes, which can be executed in a computer by using an interpreter, as well as machine codes made by a compiler. Any of the hardware devices as described above may be configured to work as one or more software modules in order to perform the operations according to various embodiments of the present disclosure, and vice versa.

Any of the modules or programming modules according to various embodiments of the present disclosure may include at least one of the above described elements, exclude some of the elements, or further include other additional elements. The operations performed by the modules, programming module, or other elements according to various embodiments of the present disclosure may be executed in a sequential, parallel, repetitive, or heuristic manner. Further, some operations may be executed according to another order or may be omitted, or other operations may be added.

According to various embodiments, in a storage medium that stores instructions, the instructions are set such that at least one process performs at least one operation when the at least one process is executed.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA.

As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

In addition, an artisan understands and appreciates that a "processor" or "microprocessor" constitute hardware in the present disclosure. Under the broadest reasonable interpretation, the appended claims constitute statutory subject matter in compliance with 35 U.S.C. § 101.

Various embodiments of the present disclosure disclosed in this specification and the drawings are merely specific examples presented in order to easily describe technical details of the present disclosure and to help the understanding of the present disclosure, and are not intended to limit the scope of the present disclosure. Therefore, it should be construed that, in addition to the embodiments disclosed herein, all modifications and changes or modified and changed forms derived from the technical idea of various embodiments of the present disclosure fall within the scope of the present disclosure.

What is claimed is:

1. An electronic device comprising:
   a variable sensing module sensing a biometric signal or a gesture; and
   a controller determining the biometric signal or the gesture,
   wherein the variable sensing module comprises a first light emitter, a second light emitter and a receiver,
   wherein the biometric signal is sensed by the receiver using the first light emitter and, the second light emitter,
   wherein the gesture is sensed by the receiver using the second light emitter except the first light emitter, and when the controller only operates the second light emitter and the receiver among the first light emitter, the second light emitter and receiver, wherein the variable sensing module is configured to execute a notification mode, a gesture and motion sensor mode and a biometric sensor mode, and wherein the variable sensing module executes the notification mode and the gesture and motion sensor mode simultaneously.

2. The electronic device of claim 1, wherein the variable sensing module further comprises:

a light emitter for emitting light;

a transmitter adjacent to the light emitter; and a receiver adjacent to the transmitter configured to receive at least a signal of the transmitter.

3. The electronic device of claim 2, wherein the variable sensing module is configured to execute at least one of:

the notification mode in which light emitted by the light emitter indicates a status of the electronic device;

the gesture and motion sensor mode in which light received by the receiver is used to sense a gesture or a motion; and the biometric sensor mode in which the transmitter transmits light information to the receiver through an object disposed against the variable sensing module to sense biometric data of a user.

4. The electronic device of claim 3, wherein controller operates the variable sensing module in the notification mode, the gesture and motion sensor mode, or the biometric sensor mode according to a user configuration setting.

5. The electronic device of claim 3, wherein the light emitter comprises a first light source that emits light of one or more of red, green, and blue light, the transmitter comprises a second light source that emits an infrared ray, and the receiver comprises a photo diode.

6. The electronic device of claim 5, wherein when the variable sensing module executes the notification mode or the gesture and motion sensor mode, the first light source emits light in the notification mode, and the second light source and the photo diode operate to perform transmission/reception in the gesture and motion sensor mode, and wherein when the variable sensing module executes a body signal sensing mode, the first light source and the second light source operate as the transmitter to measure body information, and the photo diode receives a signal from the transmitter.

7. The electronic device of claim 6, wherein the variable sensing module executes the notification mode and the gesture and motion sensor mode simultaneously, such that:

the first light source is configured to emit light of at least one of red, green, and blue light to indicate a state of the electronic device, and the second light source of the transmitter and the photo diode of the receiver operate to sense proximity of an object to the electronic device.

8. The electronic device of claim 7, further comprising a display unit, wherein:

the controller causes the display unit to activate or deactivate according a proximity of the object as sensed by the second light source and the photo diode.

9. The electronic device of claim 5, wherein the object comprises a portion of a user's body, and:

when the variable sensing module executes the biometric sensor mode, the light emitter and the transmitter are configured to operate together as a single transmission module to transmit the light information through the object, and the receiver is configured to receive the light information indicating the biometric data, the biometric data including at least one of a heart rate and a blood oxygen saturation.

10. The electronic device of claim 9, wherein when the variable sensing module executes the biometric sensor mode:

the first light source is configured to emit at least one of red and green light through the object;

the second light source is configured to emits the infrared ray through the object in tandem with the first light source; and the photo diode is configured to receive a body signal which includes the at least one of red and green light and the infrared ray as modified by passing through the object to the photo diode.

11. An electronic device comprising:

a variable sensing module sensing a biometric signal or a gesture; and a controller determining the biometric signal or gesture, wherein the controller executes a function of the electronic device in response to the biometric signal or the gesture sensed by the variable sensing module, wherein the variable sensing module comprises a first light emitter, a second light emitter and a receiver, wherein a biometric signal is sensed by the receiver using the first light emitter and, the second light emitter, wherein a gesture is sensed by the receiver using the second light emitter exception the first light emitter, and when the controller only operates the second light emitter and the receiver among the first light emitter, the second light emitter and receiver, wherein the variable sensing module is configured to execute a notification mode, a gesture and motion sensor mode and a biometric sensor mode, and wherein the variable sensing module executes the notification mode and the gesture and motion sensor mode simultaneously.

12. The electronic device of claim 11, wherein the variable sensing module comprises:

a first light source disposed on a periphery of the electronic device and configured to emit at least one visible ray of red, green, and blue light;

a second light source disposed adjacent to the first light source and configured to emit an infrared ray; and a photo diode disposed adjacent to the second light source.

13. The electronic device of claim 12, wherein a plurality of modes comprises a biometric sensor mode in which the first light source and the second light source are configured to transmit light information to the photo diode through an object disposed against the variable sensing module to sense biometric data of a user.

14. The electronic device of claim 13, wherein the plurality of modes further comprises:

the notification mode in which light emitted by the first light source indicates a status of the electronic device; and the gesture and motion sensor mode in which light received by the photo diode is used to sense a gesture or a motion.

15. The electronic device of claim 14, wherein the variable sensing module executes the notification mode and the gesture and motion sensor mode simultaneously, such that:

the first light source is configured to emit light of at least one of red, green, and blue light to indicate a state of the electronic device, and the second light source and the photo diode operate to sense proximity of an object to the electronic device.

16. The electronic device of claim 14, wherein the object comprises a portion of a user's body.

17. The electronic device of claim 16, wherein when the variable sensing module executes the biometric sensor mode, the first light source and the second light source are configured to operate together as a single transmission module to transmit the light information through the object.

18. The electronic device of claim 17, wherein the at least one of red and green light transmitted from the first light source, and the infrared ray transmitted from the second light source, are modified by passing through the object to the photo diode to generate a signal indicating the biometric data.

19. The electronic device of claim 18, wherein the biometric data includes at least one of a heart rate and a blood oxygen saturation.

* * * * *